United States Patent [19]

Sandler et al.

[11] 4,324,910
[45] Apr. 13, 1982

[54] SUBSTITUTED UREA COMPOUND CONTAINING 2,2,2-TRICHLORO-1-HYDROXYETHYL GROUP

[75] Inventors: Stanley R. Sandler, Springfield; Mabel M. Chen, Broomall, both of Pa.

[73] Assignee: Pennwalt Corporation, Philadelphia, Pa.

[21] Appl. No.: 236,374

[22] Filed: Feb. 20, 1981

Related U.S. Application Data

[63] Continuation-in-part of Ser. No. 118,298, Feb. 4, 1980, abandoned.

[51] Int. Cl.$^3$ .................. C07C 127/15; A62D 1/00
[52] U.S. Cl. ............................ 564/60; 564/30; 521/164
[58] Field of Search .................... 564/30, 60

[56] References Cited

U.S. PATENT DOCUMENTS

| | | | |
|---|---|---|---|
| 3,903,154 | 9/1975 | Singer | 564/60 X |
| 4,111,683 | 9/1978 | Singer | 564/60 X |
| 4,152,497 | 5/1979 | Miano et al. | 521/164 |
| 4,258,060 | 3/1981 | Goddard | 564/60 X |
| 4,276,387 | 6/1981 | Miano et al. | 564/60 X |

OTHER PUBLICATIONS

Smithkline Corp., CA 83:26744j, (1975).

*Primary Examiner*—Thomas A. Waltz
*Attorney, Agent, or Firm*—John S. Munday

[57] ABSTRACT

A substituted urea compound containing at least one 2,2,2-trichloro-1-hydroxyethyl group is provided which is useful as a flame retardant for polymers such as polyurethane.

6 Claims, No Drawings

SUBSTITUTED UREA COMPOUND CONTAINING 2,2,2-TRICHLORO-1-HYDROXYETHYL GROUP

BACKGROUND OF THE INVENTION

This application is a continuation-in-part of U.S. application Ser. No. 118,298 filed Feb. 4, 1980, now abandoned in the name of the same inventors.

1. Field of the Invention

This invention relates to a substituted urea compound containing at least one 2,2,2-trichloro-1-hydroxyethyl group which is useful as flame retardants.

2. Description of the Prior Art

U.S. Pat. No. 4,152,497 discloses that certain reaction products of chloral with urea, thiourea, or sulfamide are useful as reactive flame retardants for polyurethane foams. The disclosed solid mono- or dichloral urea compounds have the disadvantage of having limited solubility in polyhydroxy compounds even when prepared directly in polyols as described in copending application Ser. No. 064,656. Such flame retardant polyol solutions do not have sufficiently high chlorine contents to be useful for preparing highly flame resistant polymers.

The compound of the present invention overcomes the disadvantages of the prior art because they are much more soluble than the prior art compounds; they allow the preparation of polyol solutions that have higher chlorine content than the prior art compounds, thus making them more useful for preparing polymers with a higher degree of fire resistance such as Class 1 rigid polyurethane foams. The prior art solutions are difficult to produce with chlorine contents higher than thirty percent while the most preferred compound of this invention can be conveniently produced with higher chlorine contents. In addition, the lack of a polyol dileunt permits the compound of this invention to be used as flame retardants for various other polymers such as polystyrene, polyolefins unsaturated polyesters, and cellulosics.

STATEMENT OF THE INVENTION

A. The present invention is directed to a flame retardant composition having the formula:

$$\underset{\underset{OH}{|}}{CCl_3CHOR^4}-\underset{\underset{}{|}}{\overset{R^1}{N}}-\overset{\overset{Z}{\|}}{C}-\overset{R^2}{\underset{}{N}}-R^3 \quad (I)$$

wherein
(a) z is selected from O or S;
(b) $R^1$ and $R_2$ are selected from the group consisting of H, alkyl of 1 to 6 carbons;
(c) $R^3$ is selected from H, alkyl of 1 to 6 carbons, substituted or unsubstituted hydroxyalkyl of 2 to 4 carbons,

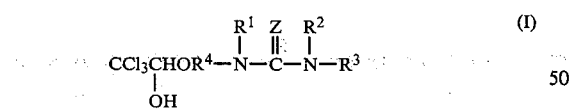

and
(d) $R^4$ is an alkylene group of 2 to 6 carbon atoms.

B. This invention also comprehends a polyurethane foam prepared from a reaction mixture which comprises a sufficient amount of the compound of paragraph A to render it flame retardant.

DEFINITIONS

Representative substituted-urea compounds useful in preparing the compound of this invention are:

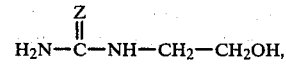

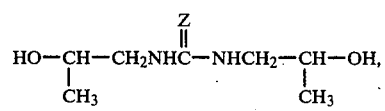

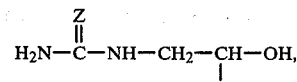

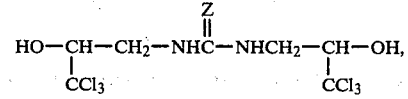

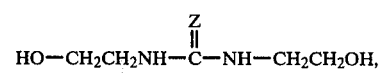

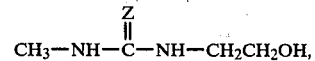

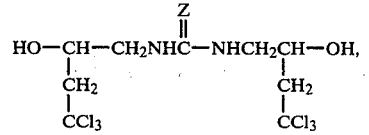

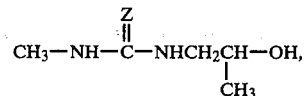

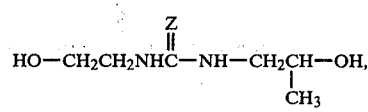

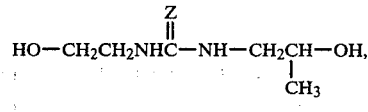

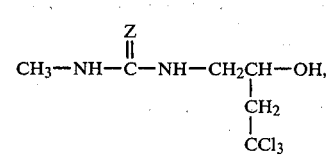

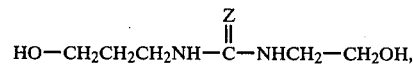

-continued

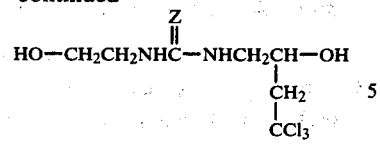

and mixtures thereof, wherein Z is oxygen or sulfur.

Preferred substituted urea compounds, and mixtures thereof, are:

-continued

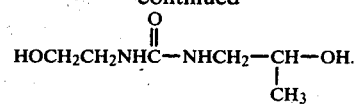

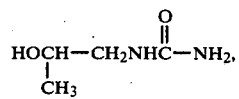

Most preferred substituted urea compounds, and mixtures, thereof are:

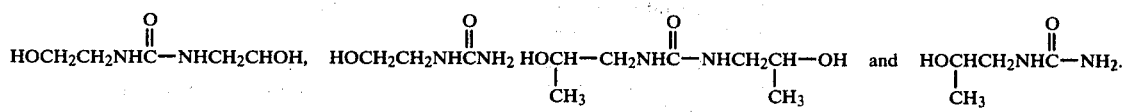

Representative compounds of the present invention are:

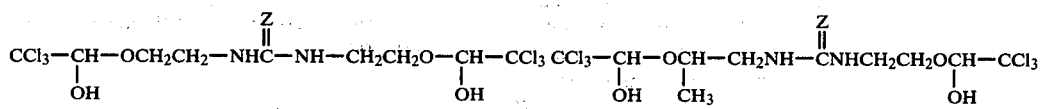

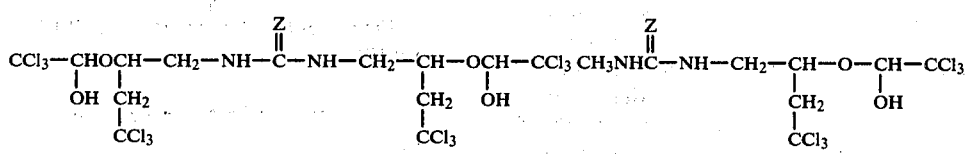

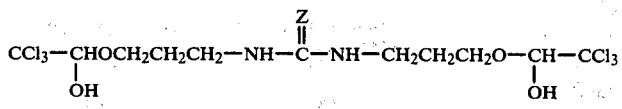

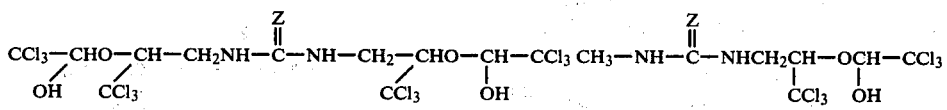

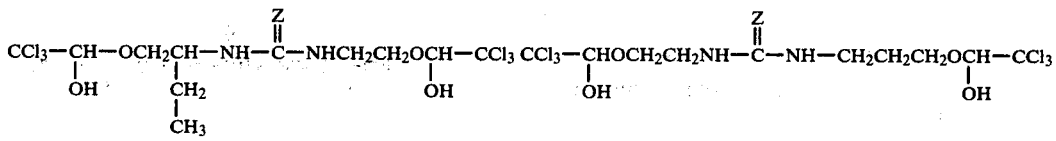

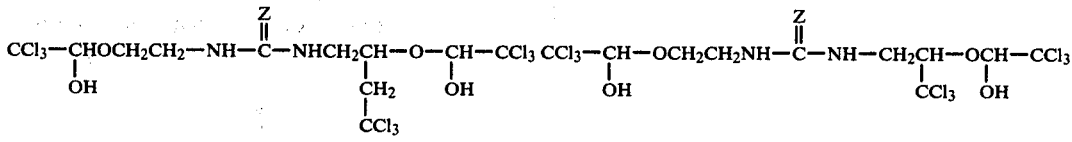

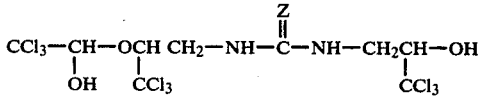

$$\underset{HOCH_2CH_2NH\overset{O}{\overset{\|}{C}}-NHCH_2CH_2OH,}{}$$

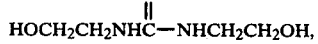

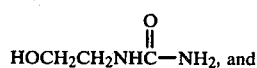

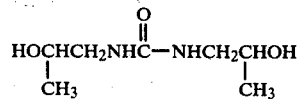

and mixtures thereof wherein Z is oxygen of sulfur.

Particularly preferred compounds of the instant invention are:

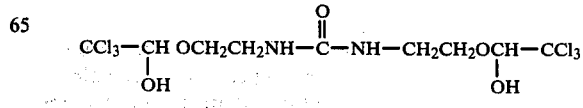

-continued

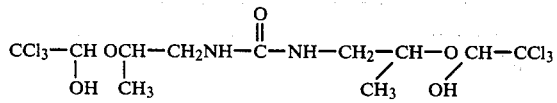

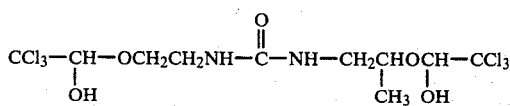

and mixtures of the above.

Most preferred compounds of this invention are:

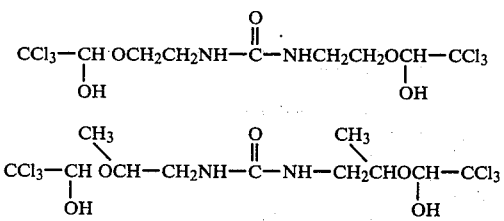

and mixtures thereof.

The compounds of this invention can be added to the polyol component used in preparing polyurethane foam in the amount of up to 100 percent of the total polyol. The preferred level of the flame-retardant compound for high-resiliency flexible polyurethane foam is 1 to 15 parts per hundred parts polyol; for rigid polyurethane foam the preferred range of the flame-retardant is 10 to 100 percent of the total polyol.

The flame-resistant compound of this invention is blended directly with all the standard components used in preparing polyurethane foam; it is also added when optional additives such as stabilizers, plasticizers, pigments, antioxidants, flame-retardants, smoke suppressants, etc. are incorporated in the foam.

The flame retardant compounds of this invention are also suitable for flame retarding other plastics such as unsaturated polyesters, polystyrene, polyolefins, acrylates, methacrylates, acrylonitrile, phenolics and isocyanurates. In addition, they are useful for flame retarding cellulosics such as paper and wood. The compounds of this invention can also be used as pesticides, herbicides, fungicides and bactericides. The compositions of this invention are also useful as intermediates in various organic synthetic preparations.

The production of polyurethanes is a well-known commercial process. Briefly, the process involves the reaction of a di- or polyisocyanate with a polyfunctional compound that may contain hydroxyl, amino, or carboxyl groups, i.e., a polyfunctional compound containing active hydrogens. The most common type of polyurethanes are formed by the reaction of toluene diisocyanate (TDI) or polymethylene polyphenylisocyanate or mixtures thereof with polyfunctional hydroxyl compounds.

EXAMPLES

Polyurethane foams described in the following examples are made by the use of disclosed flame-retardant compounds, and optionally, by the use of polyols followed by the addition of catalysts, surfactant, blowing agent (optional) and isocyanate. The components in the foams in the examples are in the measure-units of parts by weight unless otherwise indicated or a non-measure unit item such as an index. This mixture is stirred by a high-speed mixer and is poured into a mold. After the reaction is completed the foam is removed and aged at room temperature for at least seven days before testing for flammability by ASTM D-1692-74.

The compound of this invention may also contain some unreacted starting materials, and the chloral adduct of 2-oxazolidinone without detracting from their usefulness as flame retardants.

The following examples illustrate the invention and are not to be taken as a limitation thereof.

EXAMPLE 1

1,3-bis[2-(2,2,2-tricholoro-1-hydroxyethoxy)-propyl]urea

A mixture of 38 g (0.63 mole) of urea and 100 g (1.33 mole) of D,L-1-amino-2-propanol was heated at 130°-160° C. for 3 hours to form 1,3-bis(2-hydroxypropyl)urea. Without isolation, the reaction mixture was cooled to 75° C. and 196.4 g (1.33 mole) of chloral was added slowly while the temperature was maintained below 80° C. using external cooling. The reaction mixture was vigorously stirred and heated at 80° C. for 1 hour. On cooling 298 g of a clear viscous syrup product was isolated.

EXAMPLE 2

1,3-Bis[2-(2,2,2-trichloro-1-hydroxyethoxy)-ethyl]urea 50 g (0.34 mole) of diethanolurea was heated to 45° C.; 101 g (0.69 mole) of chloral was added thereto with cooling to maintain the temperature between 45°-50° C. After the addition was complete, the reaction mixture was vigorously stirred while being warmed at 45°-50° C. for an additional 2 hours. On cooling 130 g of a clear viscous liquid product was isolated.

EXAMPLE 3

1-(2,2,2-trichloro-1-hydroxyethyl)-3-[2-(2,2,2-trichloro-1-hydroxyethoxy)-ethyl]urea 52 g (0.5 mole) of monoethanolurea was heated to 80° C.; 149.0 g (1.01 mole) of chloral was added dropwise thereto between 80°-90° C. with stirring and heated between 80°-90° C. for an additional hour. On cooling, a clear viscous liquid product was obtained that weighed 200 g.

EXAMPLE 4

1-(2,2,2-trichloro-1-hydroxyethyl)-3-[2-(2,2,2-trichloro-1-hydroxyethoxy)-propyl]urea 59 g. (0.5 mole) of monoisopropanol urea was heated to 80° C.; 149.0 g (1.01 moles) of chloral was added dropwise thereto between 80°-90° C. with stirring. After the addition, the reaction mixture was stirred and heated between 80-90° C. for an additional hour. On cooling a clear viscous liquid product was obtained that weighted 205 g.

EXAMPLE 5

A rigid polyurethane foam was prepared using the composition of Example 1 as follows:

|  | Parts by Wt. |
|---|---|
| Composition of Example 1 | 23.9 |
| Multranol 4035 Polyol (Mobay)[a] | 2.7 |
| Multranol E-9221 Polyl (Mobay)[b] | 73.5 |
| DC 193 Surfactant (Dow Corning)[c] | 1.8 |
| Polycat 8 Catalyst (Abbott)[d] | 1.0 |

| | Parts by Wt. |
|---|---|
| T12 Catalyst (M&T)[e] | 0.1 |
| Isotron 11B Blowing Agent[f] (Pennwalt) | 27.0 |
| Mondur MR Isocyanate (Mobay)[g] | 124.5 |

The reactivity parameters for the foam preparation are:

| | |
|---|---|
| Cream time (sec) | 11 |
| Gel Time (sec) | 25 |
| Tack-Free Time (sec) | 39 |
| Rise Time (sec) | 62 |
| Physical Property | |
| Core Density (lb/ft$^3$) | 2.8 |
| Flammability Properties: | |
| ASTM D-1692 Inches Burned | 2.5 |
| Rate: Inches/min | 2.0 |

[a] Low viscosity polyol of hydroxyl number: 380 mg.KOH/g.
[b] A sucrose/amine based polyol hydroxyl number: 475 mg. KOH/g.
[c] A nonhydrolyzable silicone glycol copolymer
[d] Dimethyl cyclohexylamine
[e] Dibutyltin dilaurate
[f] Trichlorofluoromethane with 0.25% alloocimene as an inhibitor.
[g] Polymethylene Polyphenyl Isocyanate

EXAMPLES 6 AND 7

Rigid polyurethane foams were prepared using the composition of Example 2 as follows:

| | Ex. 7 | Ex. 8 |
|---|---|---|
| | Parts by Wt. | |
| Composition of Example 2 | 22.5 | 30.9 |
| Multranol E-9221 Polyol (Mobay) | 77.5 | 65.7 |
| DC 193 Surfactant (Dow Corning) | 1.8 | 1.8 |
| Polycat 8 Catalyst (Abbott) | 0.8 | 0.8 |
| T12 Catalyst (M&T) | 0.05 | 0.05 |
| Isotron 11B Blowing Agent (Pennwalt) | 24.3 | 27.7 |
| Mondur MR Isocyanate (Mobay) | 127.0 | 114.9 |

The reactivity parameters for the foam preparation are:

| | | |
|---|---|---|
| Cream Time (sec) | 17 | 11 |
| Gel Time (sec) | 44 | 36 |
| Tack-Free Time (sec) | 82 | 74 |
| Rise Time (sec) | 101 | 95 |
| Physical Properties: | | |
| Core Density (lb/ft$^3$) | 2.9 | 2.4 |
| Flammability Properties: | | |
| ASTM D-1692 Inches Burned | 2.8 | 1.7 |
| Rate: Inches/min | 2.0 | 2.1 |

EXAMPLE 8

A rigid polyurethane foam was prepared using no flame-retardant; the flammability test results below show that the foam burns completely (5 inches) in the ASTM D-1692 test.

| | Parts by Wt. |
|---|---|
| Multranol E-9221 (Mobay) | 100.0 |
| DC 193 | 1.8 |
| Polycat 8 | 1.0 |
| T12 | 0.1 |
| Isotron 11B | 36.0 |
| Mondur MR | 125.6 |

The reactivity parameters for the foam preparation are:

| | |
|---|---|
| Cream Time (sec) | 34 |
| Gel Time (sec) | 60 |
| Tack-Free Time (sec) | 71 |
| Rise Time (sec) | 90 |
| Physical Property: | |
| Core Density (lb/ft$^3$) | 2.7 |
| Flammability Properties: | |
| ASTM D-1692 Inches Burned (Total Burn) | 5.0 |
| Rate: Inches/min | 5.2 |

EXAMPLE 9

A rigid polyurethane foam was prepared using flame-retardant composition of Example 1 or copending application Ser. No. 064,656; although this compound provides good flame retardancy, the core density of the foam is considerably less than that based on a similar formulation obtained for the foams in Examples 5, 6 and 7.

| | |
|---|---|
| Composition of Example 1 of SN 064,656 | 60.0 |
| Multranol E-9221 (Mobay) | 40.0 |
| DC 193 Surfactant (Dow Corning) | 1.8 |
| Polycat 8 catalyst (Abbott) | 1.0 |
| T12 Catalyst (M&T) | 0.1 |
| Isotron 11B Blowing Agent (Pennwalt) | 27.0 |
| Mondur MR Isocyanate (Mobay) | 117.8 |

The reactivity parameters for the foam properties are:

| | |
|---|---|
| Cream Time (sec) | 23 |
| Gel Time (sec) | 55 |
| Tack-Free Time (sec) | 75 |
| Rise Time (sec) | 98 |
| Physical Property: | |
| Core Density lb/ft$^3$ | 1.9 |
| Flammability Properties: | |
| ASTM D-1692 Inches Burned | 2.5 |
| Rate: Inches/min | 2.5 |

EXAMPLE 10

1,3-Bis[2-(2,2,2-trichloro-1-hydroxyethoxy)ethyl]thiourea

To 98.4 g (0.6 mole) of 1,3-bis(2-hydroxyethyl)thiourea as 65° C. was slowly added 182 g (1.24 moles) of chloral while the temperature was maintained below 75° C. by means of external cooling. The reaction mixture was vigorously stirred and heated at 80° C. for 1 hour. On cooling 275 g of a viscous syrupy product was isolated.

EXAMPLE 11

To 85 g of the composition of Example 2 is added 15 g of triethylene glycol or a viscosity modifier.

EXAMPLES 12-13

Rigid polyurethane foams were prepared using the composition of Example 11 as follows:

| | Ex. 12 | Ex. 13 |
|---|---|---|
| | Parts by Wt. | |
| Composition of Example 11 | 30.0 | 40.0 |
| Multranol E-9221 Polyol (Mobay) | 70.0 | 60.0 |
| DC 193 Surfactant (Dow Corning) | 1.8 | 1.8 |
| Polycat 8 Catalyst (Abbott) | 1.0 | 1.0 |
| T12 Caralyst (M&T) | 0.1 | 0.1 |
| Isotron 11B Blowing Agent (Pennwalt) | 33.0 | 33.0 |
| Mondur MR Isocyanate (Mobay) | 110.8 | 105.9 |

The reactivity parameters for the foam preparations are:

|  |  |  |
|---|---|---|
| Cream Time (sec) | 17 | 5 |
| Gel Time (sec) | 46 | 32 |
| Tack-Free Time (sec) | 65 | 55 |
| Rise Time (sec) | 85 | 67 |
| Flammability Properties; |  |  |
| ASTM D-1692 Inches Burned | 3.2 | 2.8 |
| Rate: Inches/min | 2.8 | 3.0 |

We claim:

1. A compound having the formula:

$$CCl_3-CHOR^4-\underset{\underset{OH}{|}}{N}-\underset{\|}{\overset{Z}{C}}-\underset{|}{N}-R^3$$
(with $R^1$ on the first N and $R^2$ on the second N)

wherein:
(a) Z is selected from O or S;
(b) $R^1$ and $R^2$ are selected from the group consisting of H, alkyl of 1 to 6 carbons;
(c) $R^3$ is selected from H, alkyl of 1 to 6 carbons, hydroxyalkyl of 2 to 4 carbons;

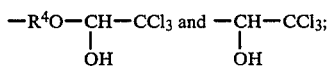

and
(d) $R^4$ is an alkylene group of 2 to 6 carbon atoms.

2. The compound of claim 1 wherein $R^1$ and $R^2$ are H, $R^3$ is

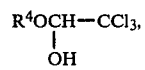

Z is O, and $R^4$ is CH2CH2.

3. The compound of claim 1 wherein $R^1$ and $R^2$ are H, $R^3$ is

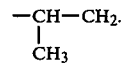

Z is O, and $R^4$ is $$-\underset{\underset{CH_3}{|}}{CH}-CH_2.$$

4. The compound of claim 1 wherein $R^1$ and $R^2$ are H, $R^3$ is HOCH2CH2, Z is O, and $R^4$ is CH2CH2.

5. The compound of claim 1 wherein $R^1$ and $R^2$ are H, $R^3$ is

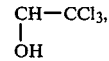

Z is O, and $R^4$ is —CH2CH2—.

6. The compound of claim 1 wherein $R^1$ and $R^2$ are H, $R^3$ is

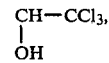

Z is O, and $R^4$ is $$-\underset{\underset{CH_3}{|}}{CH}-CH_2.$$

* * * * *